US00PP13609P2

(12) United States Plant Patent
Catt

(10) Patent No.: US PP13,609 P2
(45) Date of Patent: Feb. 25, 2003

(54) SPIREA PLANT NAMED 'WHITE GOLD'

(76) Inventor: Peter Catt, Petersfield Road, Greatham, Liss Hampshire (GB), GU33 6HA ( * ) Notice: Subject to any disclaimer, the term of this patent is extended or adjusted under 35 U.S.C. 154(b) by 0 days.

(21) Appl. No.: 09/971,478

(22) Filed: Oct. 5, 2001

(51) Int. Cl.[7] ..... A01H 5/00
(52) U.S. Cl. ..... Plt./226

(58) Field of Search ..... Plt./226, 263

*Primary Examiner*—Bruce R. Campell
*Assistant Examiner*—Annette H. Para
(74) *Attorney, Agent, or Firm*—Mark P. Bourgeois

(57) ABSTRACT

A new cultivar of Spirea named 'White Gold' that is characterized by its hardiness, compact habit, golden foliage and clusters of diminutive cream-white flowers. In combination these traits set 'White Gold' apart from all other existing varieties of Spirea known to the inventor.

3 Drawing Sheets

Botanical classification: *Spirea japonica.*
Variety denomination: 'White Gold'.

BACKGROUND OF THE INVENTION

The present invention relates to a new and distinct cultivar of Spirea, a deciduous ornamental. The new cultivar is known botanically as *Spirea japonica* and will be referred to hereinafter by the cultivar name 'White Gold'.

The breeding for a Spirea with gold leaves and white flowers began in 1993 in Hampshire, England when the inventor crossed the female parent *Spirea japonica* var. *albiflora* with the male parent *Spirea japonica* 'Candlelight' (unpatented). The resultant seedlings flowered in 1994 and because none of the yellow-leaved seedlings exhibited white flowers, a yellow seedling was selected and used as the female parent and crossed with the male parent *Spirea japonica* var. *albiflora*. As a result of this cross several seedlings were produced which had gold leaves and white flowers. When these seedlings were developed and flowering freely, a final selection was made. 'White Gold' was selected by the inventor in 1996.

The distinguishing characteristics of 'White gold' are hardiness, compact habit, diminutive cream-white flowers and golden yellow-green foliage. 'White Gold' is distinguishable from all other cultivars of *Spirea japonica* by its cream-white flowers. The inventor has no knowledge of any other cultivars of *Spirea japonica* which combine golden foliage with cream-white flowers. All other golden-foliaged cultivars of *Spirea japonica* known to the inventor exhibit pink or mauve colored flowers.

'White Gold' was first asexually propagated by the inventor in Hampshire, United Kingdom in 1996 using softwood cuttings. Since that time, under careful observation, the distinguishing characteristics have been determined stable and uniform in successive generations.

SUMMARY OF THE INVENTION

The following represent the distinguishing characteristics of the new Spirea cultivar 'White Gold'. In combination these traits set 'White Gold' apart from all other existing varieties of Spirea known to the inventor. 'White Gold' has not been tested under all possible conditions and phenotypic differences may be observed with variations in environmental, climatic, and cultural conditions, however, without any variance in genotype.

1. Spirea 'White Gold' exhibits dense clusters of cream-white flowers in summer.
2. Spirea 'White Gold' is 75 cm. in height and 75 cm. in width.
3. Spirea 'White Gold' exhibits golden yellow-green foliage.
4. Spirea 'White Gold' is winter hardy.
5. Spirea 'White Gold' exhibits a compact habit.

BRIEF DESCRIPTION OF THE DRAWINGS

The accompanying color photographs illustrate the distinguishing traits of the new Spirea cultivar 'White Gold'. The plants in the photographs are 15 months old and were grown out of doors in Arroyo Grande, Calif. in two-gallon containers.

The photograph on sheet 1 illustrates the entire plant from a side perspective.

The photograph on sheet 2 is a close-up view of the leaf and buds.

The photograph on sheet 3 illustrates flowers fully opened. All photographs are taken using conventional techniques and although foliage colors may appear different from actual colors due to light reflectance, they are as accurate as possible by conventional photography.

BOTANICAL DESCRIPTION OF THE PLANT

The following is a detailed description of the Spirea cultivar named 'White Gold'. Data was collected in Arroyo Grande, Calif. from the inventor and plants grown in two-gallon containers out of doors. The plants were approximately 15 months old at the time. Color determinations are in accordance with The Royal Horticultural Society Colour Chart except where general color terms of ordinary dictionary significance are used. The growing requirements are similar to the species. Under normal growing conditions there are no known disease problems known to the inventor.

Botanical classification: *Spirea japonica* 'White Gold'.
Common name: Bridal wreath.
Uses: Ornamental.
Parent: 'White Gold' is a hybrid resulting from the induced hybridization of the following plants:
*Female parent.*—An unnamed yellow-leaved Spirea seedling.
*Male parent.*—*Spirea japonica* var. *albiflora.*

Type: Shrub.
Vigor: Vigorous.
Habit: Compact.
Height (two-gallon): 60 cm. in height.
Width (two-gallon): 120 cm. in width.
Hardiness: USDA Zone 5.
Propagation: Softwood cuttings.
Root system: Fibrous.
Soil: Plant in well drained, moisture retentive soil that is moderately fertile.
Sunlight: Plant in full sunlight.
Plant sexuality: Bisexual.
Time to initiate roots: 2 weeks are required for an initial cutting to produce roots.
Crop time: 8–10 months are required to produce a finished one-gallon from a rooted cutting.

*Seasonal interest.*—Cream-white flowers in summer.

*Stem.*—Branching habit: Divergent. Internode length: 2–4.5 cm. between nodes. Stem diameter: 0.25 cm. in diameter. Stem length: 55 cm. in length. Shape: Cylindrical. Form: Closest to sinistrorse. Surface: Puberulent and multicostate. Texture: Suffrutescent. Stipules: Absent. Stem color: 165B.

*Foliage.*—Type: Deciduous. Leaf arrangement: Alternate. Quantity of leaves: Approximately 125 per stem. Leaf division: simple. Leaf shape: Oval. Leaf base: Cuneate. Leaf apex: Acute. Leaf venation: Palmate. Vein color (adaxial surface): 147D. Vein color (abaxial surface): 145A. Leaf surface (adaxial): Puberulent. Leaf surface (abaxial): Puberulent. Leaf attachment: Petiolate. Petiole dimensions: 3 mm. in length and 1 mm. in diameter. Petiole color: 145A. Leaf margin: Crenulate. Leaf texture: Soft and flexible. Leaf length: 2–5 cm. in length. Leaf width: 2–3.5 cm. in width. Leaf color (adaxial surface): The leaf color is influenced by the degree of sunlight and can range between 144A and 153A. Leaf color (abaxial surface): The leaf color is influenced by the degree of sunlight and can range between 144A and 153A. Foliar fragrance: Absent.

*Flower.*—Inflorescence: Terminal corymb. Quantity of flowers: Approximately 30 per corymb. Persistent or self-cleaning: Self-cleaning. Color of peduncle: 145A. Peduncle length: 2 cm. in length. Peduncle diameter: 1 mm. in diameter. Surface of peduncle: Puberulent. Diameter of corymb: 3 cm. in diameter. Shape of flower: Open campanulate. Sexuality: Bisexual. Aspect: Facing upwards. Bud shape: Globose. Bud color: 58A. Bud surface: Puberulent. Bud dimensions: 3 mm. in length and 3 mm. in diameter. Petals: Five in number. Color of petals: 155A. Shape of petal: Ovate. Fused or unfused: Petals are unfused. Dimensions of petal: 3 mm. in length and 3 mm. in width. Calyx shape: Cupulate. Calyx dimensions: 4 mm. in width and 2 mm. in length. Color of calyx: 145A. Surface of calyx: Puberulent. Sepals: Five in number. Blooming period: Spring and summer. Fragrance: Absent.

*Reproduction organs.*—Stamens: Polyandrous. Approximately 30 in number. Dimensions of stamen: 4–6 mm. in length and less 0.50 mm. in width. Color of stamen filament: 155A. Stamen attachment: Inserted at margin of calyx tube. Dimensions of anther: Less than 0.25 mm. in width and less than 0.50 cm. in length. Pollen color: 161A. Amount of pollen: Moderate. Anther color: 161A. Pistil: One. Color of pistil: 155A. Dimensions of pistil: 3 mm. in height and less than 0.50 mm. in diameter. Stigma color: 155A. Stigma: Five filaments. Dimensions of filaments: 2 mm. in length and less than 0.50 mm. in width. Style color: 155A. Ovary position: Inferior. Ovary color: 145C. Ovary shape: Globose. Ovary dimensions: 1 mm. in diameter and 1 mm. in height.

*Seed.*—Seed surface: Glabrous. Seed shape: Oval and alate. Seed color: 159A. Seed dimensions: Less than 0.50 mm. in diameter and less than 0.50 mm. in length.

I claim:

1. A new and distinct variety of Spirea plant named ‘White Gold’ as described and illustrated.

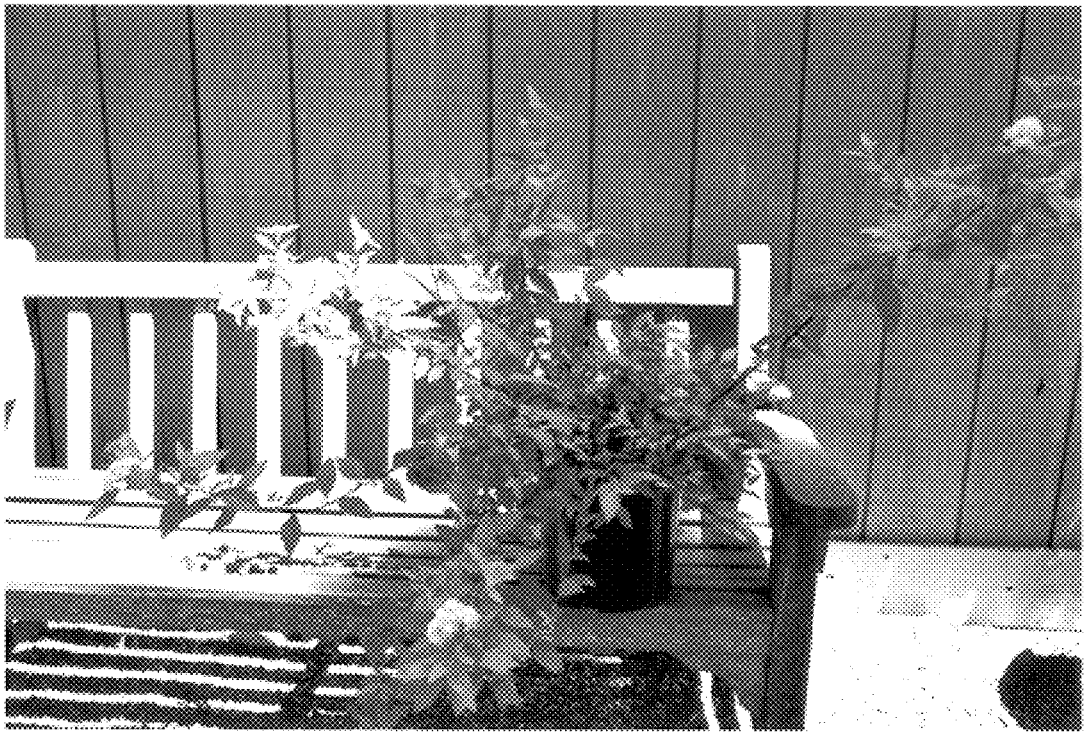

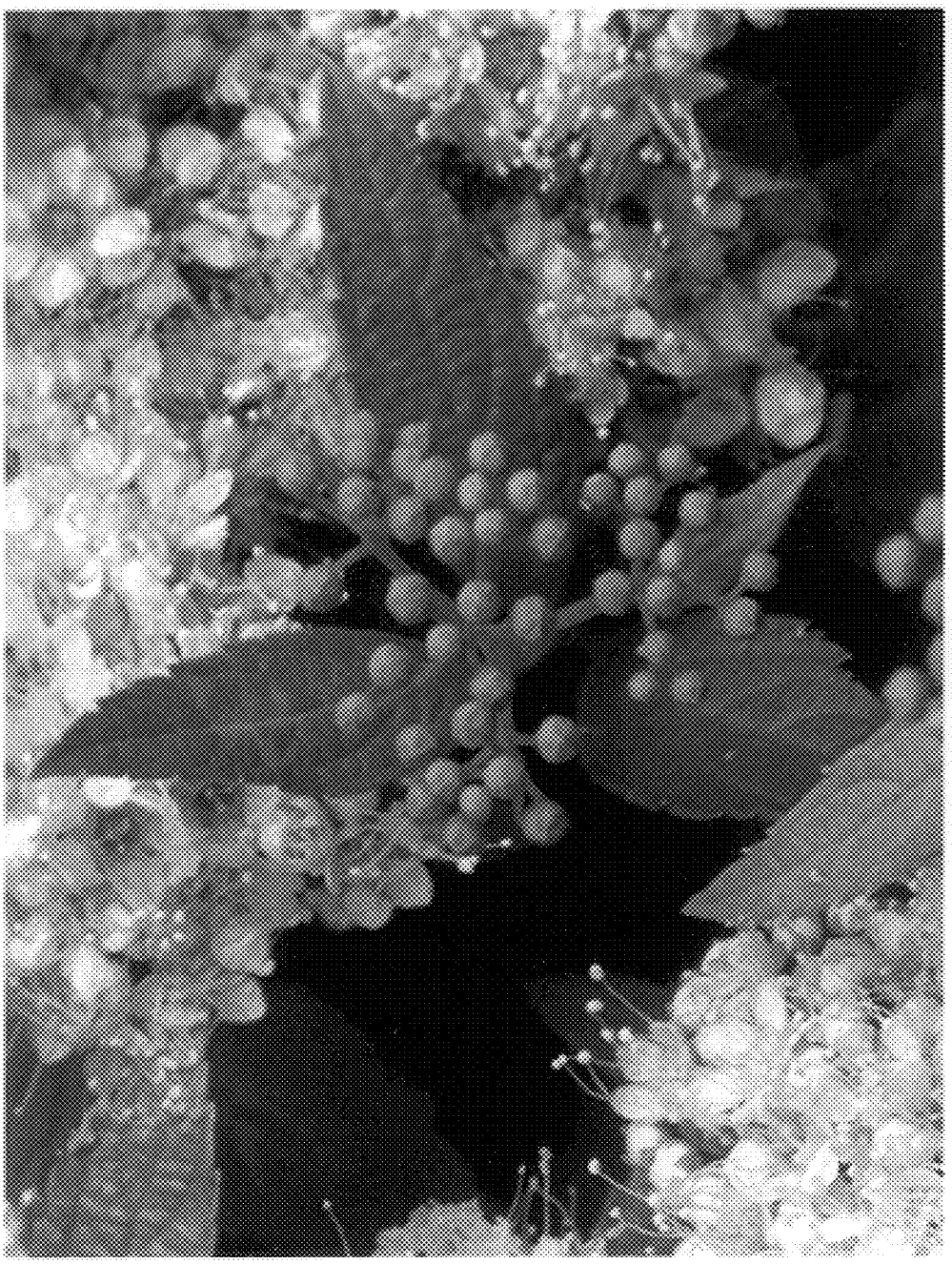

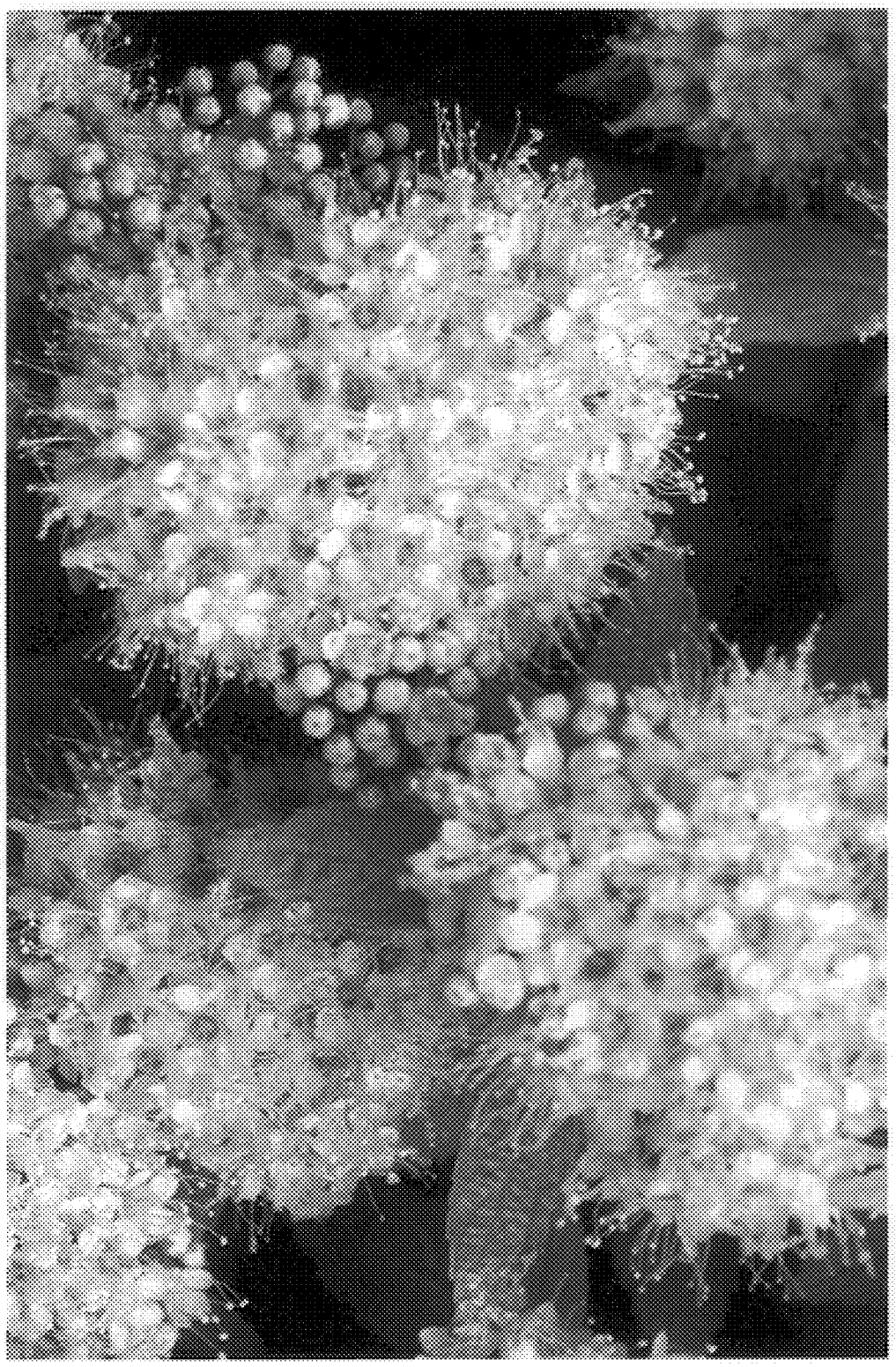

* * * * *